United States Patent
Misslitz et al.

Patent Number: 5,604,183
Date of Patent: Feb. 18, 1997

[54] CYCLOHEXENONE OXIME ETHERS

[75] Inventors: Ulf Misslitz, Neustadt; Norbert Meyer, Ladenburg; Juergen Kast, Boehl-Iggelheim; Matthias Bratz, Speyer; Albrecht Harreus, Ludwigshafen; Helmut Walter, Obrigheim; Karl-Otto Westphalen, Speyer; Matthias Gerber, Mutterstadt, all of Germany

[73] Assignee: BASF Aktiengesellschaft, Ludwigshafen, Germany

[21] Appl. No.: 523,682

[22] Filed: Sep. 5, 1995

Related U.S. Application Data

[63] Continuation of Ser. No. 190,157, Feb. 4, 1994, abandoned.

[30] Foreign Application Priority Data

Aug. 9, 1991 [DE] Germany .................. 41 26 479.7

[51] Int. Cl.[6] ............... C07C 251/50; C07C 251/52; A01N 35/10
[52] U.S. Cl. ............... 504/344; 504/270; 504/289; 548/235; 549/77; 564/256
[58] Field of Search ............... 564/256; 549/77; 548/235; 504/270, 289, 344

[56] References Cited

U.S. PATENT DOCUMENTS

| | | | |
|---|---|---|---|
| 4,432,786 | 2/1984 | Loh | 71/90 |
| 4,440,566 | 4/1984 | Luo | 71/98 |
| 4,624,696 | 11/1986 | Keil et al. | 71/88 |
| 4,909,835 | 3/1990 | Tobler | 71/103 |
| 5,022,914 | 6/1991 | Kast et al. | 71/88 |
| 5,026,899 | 6/1991 | Tobler | 560/122 |
| 5,132,462 | 7/1992 | Tobler | 568/31 |
| 5,190,573 | 3/1993 | Misslitz et al. | 504/292 |
| 8,374,609 | 12/1994 | Kast et al. | 504/344 |

FOREIGN PATENT DOCUMENTS

| | | |
|---|---|---|
| 0080301 | 6/1983 | European Pat. Off. |
| 080301 | 6/1983 | European Pat. Off. |
| 125094 | 11/1984 | European Pat. Off. |
| 238021 | 9/1987 | European Pat. Off. |
| 368227 | 5/1990 | European Pat. Off. |

Primary Examiner—Peter O'Sullivan
Attorney, Agent, or Firm—Keil & Weinkauf

[57] ABSTRACT

Cyclohexenone oxime ethers I

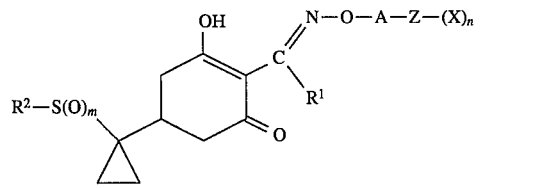

where n is from 0 to 5, m is from 0 to 2, $R^1$ is $C_1$–$C_6$-alkyl, $R^2$ is $C_1$–$C_4$-alkyl or benzyl, A is unsubstituted or substituted $C_1$–$C_6$-alkylene, unsubstituted or substituted $C_3$–$C_6$-alkenylene, unsubstituted or substituted $C_3$–$C_6$-alkynylene or an unsubstituted or substituted $C_3$–$C_6$-alkylene or $C_4$–$C_6$-alkenylene chain, where in each case a methylene group may be replaced with O, S, SO, $SO_2$ or $\dot{=}N(R^a)$—, $R^a$ is H, $C_1$–$C_4$-alkyl, $C_3$–$C_6$-alkenyl or $C_3$–$C_6$-alkynyl, Z is phenyl, a 5-membered heteroaromatic radical or a 6-membered heteroaromatic radical having from 1 to 4 nitrogen atoms, X is $NO_2$, CN, halogen, $C_1$–$C_4$-alkyl, $C_1$–$C_4$-haloalkyl, $C_1$–$C_4$-alkoxy, $C_1$–$C_4$-alkylthio, $C_1$–$C_4$-haloalkoxy, COOH, $C_1$–$C_4$-alkoxycarbonyl, unsubstituted or substituted benzyloxycarbonyl, unsubstituted or substituted phenyl, unsubstituted or substituted pyridyl or —$NR^bR^c$, $R^b$ is H, $C_1$–$C_4$-alkyl, $C_3$–$C_6$-alkenyl or $C_3$–$C_6$-alkynyl and $R^c$ is H, $C_1$–$C_4$-alkyl, $C_3$–$C_6$-alkenyl, $C_3$–$C_6$-alkynyl, $C_1$–$C_6$-acyl or unsubstituted or substituted benzoyl, and the agriculturally useful salts and esters of $C_1$–$C_{10}$-carboxylic acids and inorganic acids are suitable as herbicides.

4 Claims, No Drawings

CYCLOHEXENONE OXIME ETHERS

This application is a continuation of application Ser. No. 08/190,157, filed on Feb. 4, 1994, now abandoned, which is a 371 of PCT/EP92/01744, filed Aug. 5, 1992.

The present invention relates to novel cyclohexenone oxime ethers of the general formula I

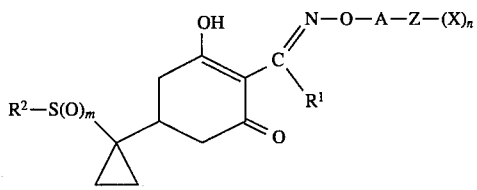

in which the variables have the following meaning:

n is from 0 to 5;
m is from 0 to 2;
$R^1$ is $C_1$–$C_6$-alkyl;
$R^2$ is $C_1$–$C_4$-alkyl or benzyl;
A is $C_1$–$C_6$-alkylene, $C_3$–$C_6$-alkenylene or $C_3$–$C_6$-alkynylene, where these groups may carry from one to three $C_1$–$C_3$-alkyl groups and/or halogen atoms,
or a $C_3$–$C_6$-alkylene or $C_4$–$C_6$-alkyenylene group which, if desired, is substituted by from one to three $C_1$–$C_3$-alkyl groups and in which one methylene group is replaced with an oxygen or sulfur atom, a sulfoxyl or sulfonyl group or a group —N($R^a$)—, where
$R^a$ is hydrogen, $C_1$–$C_4$-alkyl, $C_3$–$C_6$-alkenyl or $C_3$–$C_6$-alkynyl;
Z is phenyl, a 5-membered heteroaromtic radical having from one to three nitrogen atoms and/or one oxygen or sulfur atom or a 6-membered heteroaromatic radical having from one to four nitrogen atoms, and
X is nitro, cyano, halogen, $C_1$–$C_4$-alkyl, partially or completely halogenated $C_1$–$C_4$-alkyl, $C_1$–$C_4$-alkoxy, $C_1$–$C_4$-alkylthio, partially or completely halogenated $C_1$–$C_4$-alkoxy, carboxyl, $C_1$–$C_4$-alkoxycarbonyl, benzyloxycarbonyl, phenyl or pyridyl, where the aromatic radicals may be unsubstituted or carry from one to three of the following substituents: nitro, cyano, halogen, $C_1$–$C_4$-alkyl, partially or completely halogenated $C_1$–$C_4$-alkyl, $C_1$–$C_4$-alkoxy, $C_1$–$C_4$-alkylthio, partially or completely halogenated $C_1$–$C_4$-alkoxy, carboxyl, $C_1$–$C_4$-alkoxycarbonyl, benzyloxycarbonyl or an amino group —$R^bR^c$, where
$R^b$ is hydrogen, $C_1$–$C_4$-alkyl, $C_3$–$C_6$-alkenyl or $C_3$–$C_6$-alkynyl and
$R^c$ is hydrogen, $C_1$–$C_4$-alkyl, $C_3$–$C_6$-alkenyl, $C_3$–$C_6$-alkynyl, $C_1$–$C_6$-acyl or benzoyl which may be unsubstituted or in its turn carry from one to three of the following radicals: nitro, cyano, halogen, $C_1$–$C_4$-alkyl, $C_1$–$C_4$-alkoxy, $C_1$–$C_4$-alkylthio, $C_1$–$C_4$-haloalkyl, $C_1$–$C_4$-haloalkoxy and/or $C_1$–$C_4$-alkoxycarbonyl,
and their agriculturally useful salts and esters of $C_1$–$C_{10}$-carboxylic acids and inorganic acids.

The present invention furthermore relates to herbicides which contain these compounds as active ingredients and a method for controlling undesirable plant growth.

The literature has already disclosed herbicidal cyclohexanediones of the general formula I'

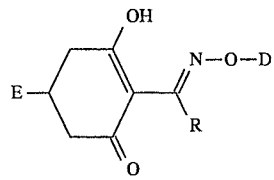

where E and D have, inter alia, the following meanings:
U.S. Pat. No. 4,440,566 (D=benzyl; E=2-ethylthiopropyl);
EP-A 238 021 and EP-A 125 094 (D=benzyl or but-2-enyl; E=a substituted 5-membered hetaryl radical);
EP-A 80 301 (D=benzyl or but-2-enyl; E=substituted phenyl);
EP-A 177 913 (D=2-thenyl or 3-thenyl; E=a substituted 5-membered to 7-membered heterocyclic structure);
U.S. Pat. No. 4,432,786 (D=5-chloro-2-thenyl; E=substituted phenyl);
EP-A 243 313 (D=(E)-3-chloroprop-2-enyl; E=1-methylthiocycloprop-1-yl).

Furthermore, DE-A 38 38 309 describes in general terms cyclohexenone oxime ethers of the type comprising the compounds I, which ethers have herbicidal activity and in which, inter alia, E is a substituted 5-membered to 7-membered heterocyclic structure and D is a substituted 4-phenylbutylene or 4-phenylbutenylene radical.

It was an object of the present invention to synthesize cyclohexenone oxime ethers which, compared with the known members of this class of substances, have greater selectivity in the control of weeds in gramineous crops, such as rice and corn.

Accordingly this object is achieved by the cyclohexenone oxime ethers I defined at the outset, which have a good herbicidal action preferably against species from the grass family (*Gramineae*). They are tolerated and hence selective in broad-leaved crops and in monocotyledon plants which are not members of the *Gramineae*. They include compounds which are also selective in gramineous crops and at the same time control undesirable grasses.

The cyclohexenone oxime ethers of the formula I are obtainable by various methods, preferably in a conventional manner from already known derivatives of the formula II (EP-A 243 313) and the corresponding hydroxylamines of the formula III (EP-A 169 521).

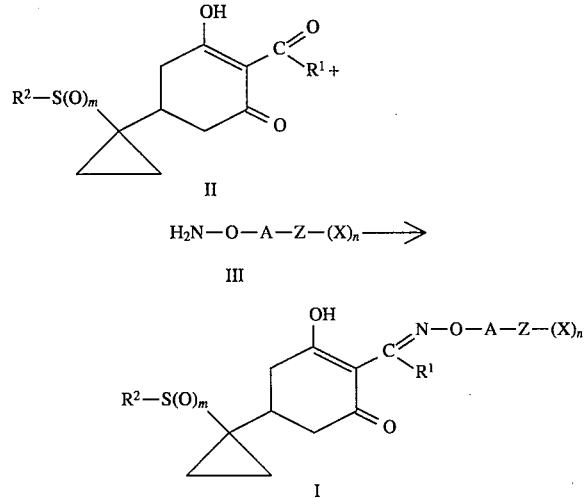

The reaction is advantageously carried out in the heterogeneous phase in a solvent at an adequate temperature below about 80° C. in the presence of a base, the hydroxylamine III preferably being used in the form of the ammonium salt.

Examples of suitable bases are carbonates, bicarbonates, acetates, alcoholates or oxides of alkali or alkaline earth metals, in particular sodium hydroxide, potassium hydroxide, magnesium oxide and calcium oxide, as well as organic bases, such as pyridine and tertiary amines, eg. triethylamine. The base is added, for example, in an amount of from 0.5 to 2 mol equivalents, based on the ammonium compound.

Examples of suitable solvents are dimethyl sulfoxide; alcohols, such as methanol, ethanol and isopropanol; aromatic hydrocarbons, such as benzene and toluene; chlorohydrocarbons, such as chloroform and 1,2-dichloroethane; aliphatic hydrocarbons, such as hexane and cyclohexane; esters, such as ethyl acetate, and ethers, such as diethyl ether, dioxane and tetrahydrofuran. The reaction is preferably carried out in methanol using sodium bicarbonate as the base.

The reaction is complete after a few hours. The product can be isolated, for example, by evaporating down the mixture, partitioning the residue between methylene chloride and water and distilling off the solvent under reduced pressure.

However, it is also possible to use the free hydroxylamine base directly, for example in the form of an aqueous solution, for this reactions a single-phase or two-phase reaction mixture is obtained, depending on the solvent used for the compound II.

Examples of suitable solvents for this variant are alcohols, such as methanol, ethanol, isopropanol and cyclohexanol; aliphatic and aromatic hydrocarbons and chlorohydrocarbons, such as hexane, cyclohexane, methylene chloride, toluene and dichloroethane; esters, such as ethyl acetate; nitriles, such as acetonitrile, and cyclic ethers, such as dioxane and tetrahydrofuran.

No special conditions with regard to the pressure are required; in general, the reaction is therefore carried out at atmospheric pressure.

The novel cyclohexenone oxime ethers I are evidently acidic, ie. they can form salts of alkali metal or alkaline earth metal compounds and enol esters.

Alkali metal salts of the compounds I can be obtained by treating the 3-hydroxy compounds with sodium hydroxide, potassium hydroxide or sodium or potassium alcoholate in aqueous solution or in an organic solvent, such as methanol, ethanol, acetone and toluene.

Other metal salts, such as manganese, copper, zinc, iron, calcium, magnesium and barium salts, can be prepared from the sodium salts in a conventional manner, as can ammonium and phosphonium salts by means of ammonia, phosphonium, sulfonium or sulfoxonium hydroxides.

The hydroxylamines III are generally obtained by a number of known process steps, starting from known intermediates:

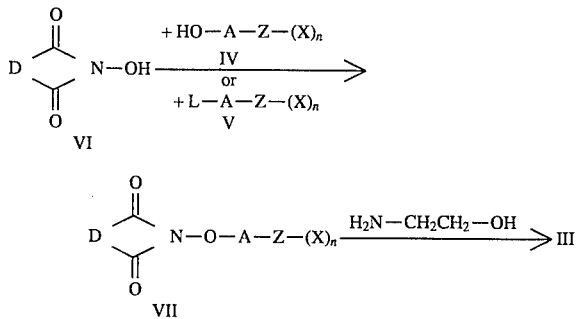

L is a leaving group, for example halogen, such as chlorine, bromine and iodine, or $CH_3SO_2$—O—.

The alkylating agents required for the synthesis of the novel hydroxylamines of the formula III can be prepared by conventional methods [cf. Rearrangement of cyclopropylhetarylcarbinols: J. Heterocycl. Chem. 14 (1976), 525, JP 55 051 004, JP 55 047 601; Houben-Weyl: Methoden der Organischen Chemie, Volume 4/3, page 424 et seq.; Coupling of metallized heterocycles with 1,ω-dibromoalkanes: DE-A 28 21 409 and Chem. Ber. 114 (1981), 3667 and 3674; Heteroatom-interrupted alkylating agents: DE-A 34 37 919; Tetrahedron Lett. 28 (1979), 2639, Org. Synth. Coll. Vol. 1 (1944), 436; DE-A 26 54 646; DE-A 2 714 561; J. Org. Chem. 52 (1987), 3587; DE-A 94 88 71; DE-A 94 88 72; J. Med. Chem. 26 (1983), 1570; Synthesis (1983), 675 and J. Org. Chem. 48 (1983), 4970].

If desired, the alkylating agents V can be obtained [cf. Houben-Weyl, Methoden der Organischen Chemie, Volume 5/3, page 862 et seq. and page 899 et seq. and ibid., Volume 5/4, page 361 et seq.] in a conventional manner from the carbinols IV [Coupling of aryl and hetaryl iodides and bromides with 1,ω-alkenols or 1,ω-alkynols in the presence of palladium catalysts: Tetrahedron Lett. 24 (1975), 4467; Tetrahedron 35 (1979), Chem. Lett. (1977), 423; Houben-Weyl: Methoden der Organischen Chemie, Volume 13/9B, page 964 et seq.].

The alkylating agent V and, if desired, also the carbinol IV are preferably coupled by the Mitsunobu method [Synthesis (1981), 1; J. Med. Chem. 33 (1990), with a cyclic hydroxyimide VI, and the resulting protected hydroxylamine derivative VII is cleaved to give the free hydroxylamine III, for example with 2-aminoethanol.

In the cyclic hydroxyimides VI, D is, for example, $C_2$- or $C_3$-alkylene, $C_2$-alkenylene or a 5-membered or 6-membered ring which contains not more than 3 double bonds and may contain one nitrogen atom, for example phenylene, pyridinylene, cyclopentylene and cyclohexylene or cyclohexenylene. Examples of suitable substances are the following:

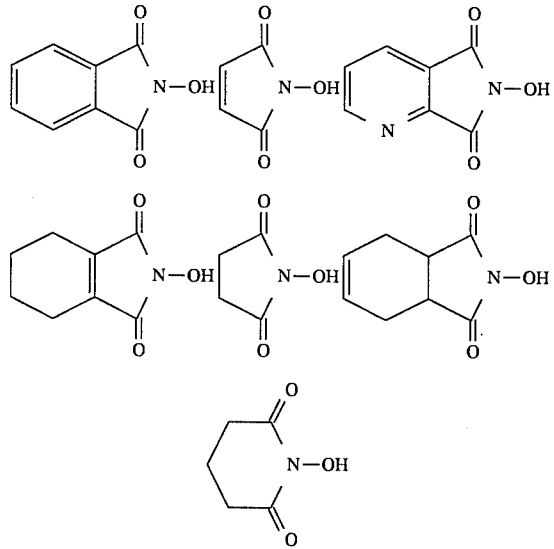

The reaction of the compounds V with the hydroxyimides VI is advantageously carried out in the presence of a base. All bases which are capable of deprotonating the hydroxyimides VI without attacking the imide system are in principle suitable. These are in particular the so called nonnucleophilic bases.

Examples are mineral bases, such as alkali metal and alkaline earth metal carbonates, and alkali metal and alkaline earth metal bicarbonates, and organic bases, such as aliphatic, cycloaliphatic and aromatic tertiary amines. Mixtures of these bases may also be used.

Examples of individual compounds are the following bases: sodium carbonate, potassium carbonate, magnesium carbonate, calcium carbonate, barium carbonate, bicarbonates of these metals, trimethylamine, triethylamine, tributylamine, ethyldiisopropylamine, N,N-dimethylaniline, 4-N,N-dimethylaminopyridine, diazabicyclooctane, diazabicycloundecane, N-methylpiperidine, 1,4-dimethylpiperazine, pyridine, quinoline, bipyridine and phenanthroline. The economical bases sodium carbonate and potassium carbonate are preferred.

The base is added in general in equivalent amounts up to an excess of 5 equivalents, based on the hydroxyimide. A larger excess is possible but has no additional advantages. It is also possible to use a smaller amount of base. However, from 1 to 3, in particular from 1 to 2, equivalents, based on the hydroxyimide VI, of the base are preferably used.

The use of nucleophilic bases, such as alkali metal and alkaline earth metal hydroxides, in particular sodium hydroxide and potassium hydroxide, is also possible. In this case, it is advantageous to use the base in equivalent amounts, based on the hydroxyimide VI, in order to prevent a nucleophilic attack by the hydroxyl ions on the carbonyl function of the imide group.

The starting compounds V are advantageously reacted with the hydroxyimides VI in a solvent which is inert under the reaction conditions. Examples of advantageous solvents are polar aprotic solvents, such as dimethylformamide, N-methylpyrrolidone, dimethyl sulfoxide, sulfolane and cyclic ureas. The amount of solvent is in general not critical.

The reaction of the starting compounds V with the hydroxyimides VI may also be carried out using phase transfer catalysis. In this case, solvents which form two phases with water, preferably chlorohydrocarbons, are used. Suitable phase transfer catalysts are the quaternary ammonium and phosphonium salts, polyethylene glycols, polyethylene glycol ethers and crown ethers, which are conventionally used for such purposes and are described in, for example, Dehmlow et al., Phase Transfer Catalysis, pages 37–45 and 86–93, Verlag Chemie, Weinheim 1980.

The phase transfer catalysts are advantageously used in amounts of from 1 to 10, preferably from 3 to 5, % by volume, based on the volume of the reaction mixture.

The reaction of the starting compounds V with the hydroxyimides VI is carried out in general at from 0° to 140° C., preferably from 2° to 100° C., in particular from 40° to 80° C. In an advantageous procedure, the hydroxyimide VI is initially taken together with the base in the solvent and the starting material V is metered into this solution. It may prove advantageous to add the hydroxyimide at a lower temperature, for example at from 0° to 50° C., and to heat the reaction mixture to the actual reaction temperature only after this addition.

After the end of the reaction, water is advantageously added to the cooled reaction mixture, the resulting hydroxylamine derivatives VII separating out as crystalline solids or as oils. The hydroxylamine derivatives obtained in this manner can, if desired, be further purified by recrystallization or by extraction.

The hydroxylamine derivatives VII may be temporarily scored or converted immediately into the hydroxylamines III (having free amino groups).

This conversion can be carried out by conventional methods, as described in, for example, DE-A 36 15 973 and the publications cited therein. The process according to DE-A 36 15 973 is preferably used, in which the hydroxylamines III are liberated by means of ethanolamine. The liberation of the hydroxylamines III with the aid of other bases, such as aqueous mineral bases, amines, hydrazines, hydroxylamines or aqueous acids, is also possible.

The hydroxylamines III can be isolated from the reaction mixtures obtained in these processes by conventional working-up methods, for example by extraction or by crystallization. To increase the tendency of these hydroxylamines to crystallize, it may often be advantageous to convert them into their salts with mineral acids or organic acids. For this purpose, dilute solutions of these acids are generally reacted with the hydroxylamines, advantageously in approximately equivalent amounts. As in the case of the hydroxylamines III having a free amino group, the resulting hydroxylammonium salts can be further processed directly to the herbicides of the formula I or, if desired, stored.

The cyclohexenone oxime ethers I may be obtained in the preparation as isomer mixtures, both E/Z isomer mixtures and enantiomer or diastereoisomer mixtures being possible. The isomer mixtures can, if desired, be separated by methods conventional therefor, for example by chromatography or by crystallization.

The cyclohexenone oxime ethers I can be represented in a plurality of tautomeric forms, and the present invention relates to all of them.

With regard to the biological activity, preferred cyclohexenone oxime ethers of the formula I are those in which the substituents have the following meanings:

n is from 0 to 5, in particular from 0, 1 or 2 or, where Z is phenyl and X is in each case halogen, from 0 to 5;

when Z is a heterocyclic structure, the maximum possible value of n corresponds to the number of substitutable ring members; in the case of a plurality of radicals X, the subtituents may be identical or different;

m is from 0 to 2, preferably 0;

$R^1$ is $C_1$–$C_6$-alkyl, such as methyl, ethyl, propyl, n-butyl, in particular ethyl and propyl;

$R^2$ is $C_1$–$C_4$-alkyl, such as methyl, ethyl, propyl, n-butyl, in particular methyl;

A is $C_1$–$C_6$-alkylene, $C_3$–$C_6$-alkenylene or $C_3$–$C_6$-alkynylene, such as methylene, ethylene, propylene, butylene, pentylene or hexylene; propenylene, prop-2-enylene, butenylene, but-2-enylene, but-3-enylene, pentenylene, pent-2-enylene, pent-3-enylene, pent-4-enylene, hexenylene, hex-2-enylene, hex-3-enylene, hex-4-enylene or hex-5-enylene; prop-2-ynylene, but-2-ynylene, but-3-ynylene, pent-2-ynylene, pent-3-ynylene, pent-4-ynylene, hex-2-ynylene, hex-3-ynylene, hex-4-ynylene or hex-5-ynylene and may be substituted by from one to three methyl or ethyl radicals and/or fluorine or chlorine atoms; in the case of the unsaturated chains, both the cis and the trans form may occur; propylene, butylene, prop-2-enylene, but-2-enylene, but-3-enylene and but-3-ynylene are particularly preferred;

$C_3$–$C_6$-alkylene or $C_4$–$C_6$-alkenylene in which a methylene group is replaced with an oxygen or sulfur atom, a sulfoxyl or sulfonyl group or —N($R^a$)—, such as 3-oxapropylene, 3-azapropylene, 3-thiapropylene, 3-oxo-3-thiapropylene, 3,3-dioxo-3-thiapropylene, 3-oxabutylene, 3-azabutylene, 4-thiabutylene, 4-oxo-4-thiabutylene, 4,4-dioxo-4-thiabutylene, 4-oxabut-2-enylene, 4-azabut-2-enylene, 4-thiabut-2-enylene, 3-oxapentylene, 3-azapentylene, 3-thiapentylene, 3-oxo-3-thiapentylene, 3,3-dioxo-3-thiapentylene, 4-oxapentylene, 4-azapentylene, 4-thiapentylene, 4-oxo-4-thiapentylene, 4,4-dioxo-4-thiapentylene, 5-oxapentylene, 5-azapentylene, 5-thiapentylene, 5-oxo-5-thiapentylene, 5,5-dioxo-5-thiapentylene, 5-oxapent-3-enylene, 5-azapent-3-enylene, 5-thiapent-3-enylene, 3-oxahexylene, 3-azahexylene, 3-thiahexylene, 3-oxo-3-thiahexylene, 3,3-dioxo-3-thiahexylene, 4-oxahexylene, 4-azahexylene, 4-thiahexylene, 4-oxo-4-thiahexylene, 4,4-dioxo-4-thiahexylene, 5-oxahexylene, 5-azahexylene, 5-thiahexylene, 5-oxo-5-thiahexylene, 5,5-dioxo-5-thiahexylene, 6-oxahexylene, 6-azahexylene, 6-thiahexylene, 6-oxo-6-thiahexylene, 6,6-dioxo-6-thiahexylene, 6-oxahex-4-enylene, 6-azahex-4-enylene or 6-thiahex-4-enylene, which may be substituted by from one to three methyl or ethyl radicals; in the case of the unsaturated chains, both the cis and the trans form may occur; 3-oxapropylene, 2-methyl-3-oxapropylene, 3-oxabutylene and 4-oxabutylene are particularly preferred;

$R^a$ is hydrogen;

$C_1$–$C_4$-alkyl, such as methyl, ethyl, n-propyl, 1-methylethyl, n-butyl, 1-methylpropyl, 2-methylpropyl or 1,1-dimethylethyl, in particular methyl or ethyl;

$C_3$–$C_6$-alkenyl, such as 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,2-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl, in particular 2-propenyl and 2-butenyl;

$C_3$–$C_6$-alkynyl, such as 2-propynyl, 2-butynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 3-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl or 1-ethyl-1-methyl-2-propynyl, in particular 2-propynyl and 2-butynyl;

Z is phenyl, 5-membered hetaryl, such as furanyl, pyrrolyl, thienyl, imidazolyl, pyrazolyl, isoxazolyl, oxazolyl, isothiazolyl, thiazolyl, oxadiazolyl, thiadiazolyl or triazolyl, in particular furanyl and thienyl, or 6-membered hetaryl, such as pyridyl, pyridazyl, pyrimidyl, pyrazyl, triazyl, tetrazyl, in particular pyridyl and pyrimidyl;

X is nitro, cyano, halogen, such as fluorine, chlorine, bromine and iodine, in particular fluorine and chlorine;

$C_1$–$C_4$-alkyl, such as methyl, ethyl, n-propyl, 1-methylethyl, n-butyl, 1-methylpropyl, 2-methylpropyl and 1,1-dimethylethyl, in particular methyl and 1,1-dimethylethyl, $C_1$–$C_4$-alkoxy, such as methoxy, ethoxy, n-propoxy, 1-methylethoxy, n-butoxy, 1-methylpropoxy, 2-methylpropoxy or 1,1-dimethylethoxy, in particular methoxy, ethoxy, 1-methylethoxy and 1,1-dimethylethoxy, $C_1$–$C_4$-alkylthio, such as methylthio, ethylthio, propylthio, 1-methylethylthio, butylthio, 1-methylpropylthio, 2-methylpropylthio and 1,1-dimethylethylthio, in particular methylthio and ethylthio, $C_1$–$C_4$-haloalkyl, such as fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluoroethyl, 2,2-dichloro-2-fluoroethyl, 2,2,2-trichloroethyl, pentafluoroethyl and 3-chloropropyl, in particular difluoromethyl, trifluoromethyl, 2,2,2-trifluoroethyl and pentafluoroethyl, $C_1$–$C_4$-haloalkoxy, such as difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy and pentafluoroethoxy, in particular trifluoromethoxy, carboxyl, $C_1$–$C_4$-alkoxycarbonyl, such as methoxycarbonyl, ethoxycarbonyl, n-propoxycarbonyl, 1-methylethoxycarbonyl, n-butoxycarbonyl and 1,1-dimethylethoxycarbonyl, in particular methoxycarbonyl, ethoxycarbonyl and 1,1-dimethylethoxycarbonyl, especially methoxycarbonyl, as well as benzyloxycarbonyl, phenyl and pyridyl, where the aromatic radicals are in each case unsubstituted or in turn may carry from one to three of the following radicals: nitro, cyano, carboxyl, benzyloxycarbonyl, halogen as stated above in general and in particulars $C_1$–$C_4$-alkyl as stated above, in particular methyl, ethyl and 1-methylethyl; $C_1$–$C_4$-alkoxy as stated above, in particular methoxy and ethoxy; $C_1$–$C_4$-alkylthio as stated above, in particular methylthio; $C_1$–$C_4$-haloalkyl as stated above, in particular trifluoromethyl; $C_1$–$C_4$-haloalkoxy as stated above, in particular difluoromethoxy and trifluoromethoxy, and/or $C_1$–$C_4$-alkoxycarbonyl as stated above, in particular methoxycarbonyl and ethoxycarbonyl, or an amino group —$NR^bR^c$, where $R^b$ is hydrogen, $C_1$–$C_4$-alkyl, $C_3$–$C_6$-alkenyl and $C_3$–$C_6$-alkynyl as stated in general and in particular for $R^a$ and $R^c$ is hydrogen, $C_1$–$C_4$-alkyl, $C_3$–$C_6$-alkenyl or $C_3$–$C_6$-alkynyl as stated in general and in particular for $R^a$;

$C_1$–$C_6$-acyl, such as acetyl, propionyl, butyryl, 2-methylpropionyl, pentanoyl, 2-methylbutyryl, 3-methylbutyryl, 2,2-dimethylpropionyl, hexanoyl, 3-methylpentanoyl, 3-methylpentanoyl, 4-methylpentanoyl, 2,2-dimethylbutyryl, 2,3-dimethylbutyryl, 3,3-dimethylbutyryl and 2-ethylbutyryl, in particular acetyl and propionyl, or benzoyl, where the aromatic radical may be unsubstitued or furthermore carry from one to three radicals selected from a group consisting of nitro, cyano, carboxyl, benzyloxycarbonyl, halogen as stated above in general and in particular, $C_1$–$C_4$-alkyl as stated above, in particular methyl, $C_1$–$C_4$-alkoxy as stated above, in particular methoxy or ethoxy, $C_1$–$C_4$-alkylthio as stated above, in particular methylthio, $C_1$–$C_4$-haloalkyl as stated above, in particular trifluoromethyl, $C_1$–$C_4$-haloalkoxy as stated above, in particular difluoromethoxy and trifluoromethoxy, and $C_1$–$C_4$-alkoxycarbonyl as stated above, in particular methoxycarbonyl and ethoxycarbonyl.

Particularly preferred cyclohexenone oxime ethers of the formula I are shown in Table 1 below.

TABLE 1

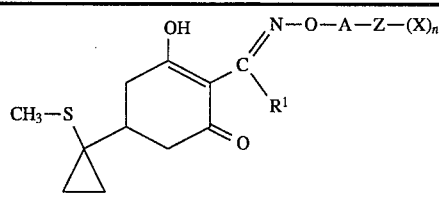
I ($R^2-S(O)_m- = CH_3-S-$)

| | $R^1$ | A | $Z (X)_n$ | Physical data ($^1$H-NMR [ppm]; mp. [°C.]) |
|---|---|---|---|---|
| 1.01 | Ethyl | trans-$CH_2CH_2CH=CH-$ | 4-Fluorophenyl | 2,13(s, 3H); 6,10(dt, 1H); 6,43(d, 1H); 7,00(m, 2H); 7,30(m, 2H) |
| 1.02 | n-Propyl | trans-$CH_2CH_2CH=CH-$ | 4-Fluorophenyl | 2,15(s, 3H); 6,10(dt, 1H); 6,45(d, 1H); 7,00(m, 2H); 7,30(m, 2H); |
| 1.03 | Ethyl | trans-$CH_2CH_2CH=CH-$ | 4-Chlorophenyl | 2,13(s, 3H); 6,20(dt, 1H); 6,43(d, 1H); 7,27(s, 4H) |
| 1.04 | n-Propyl | trans-$CH_2CH_2CH=CH-$ | 4-Chlorophenyl | 2,15(s, 3H); 6,20(dt, 1H); 6,45(d, 1H); 7,30(s, 4H) |
| 1.05 | Ethyl | $-CH_2CH_2CH_2CH_2-$ | 4-Fluorophenyl | 2,13(s, 3H); 6,95(m, 2H); 7,10(m, 2H) |
| 1.06 | n-Propyl | $-CH_2CH_2CH_2CH_2-$ | 4-Fluorophenyl | 2,15(s, 3H); 4,10(m, 2H); 6,95(m, 2H); 7,10(m, 2H) |
| 1.07 | Ethyl | $-CH_2CH_2-O-$ | 4-Fluorophenyl | 2,13(s, 3H), 6,80–7,10(m, 2H) |
| 1.08 | n-Propyl | $-CH_2CH_2-O-$ | 4-Fluorophenyl | 2,15(s, 3H); 4,20(m, 2H); 4,43(m, 2H); 6,80–7,10(m, 4H) |
| 1.09 | Ethyl | $-CH_2CH_2CH_2-O-$ | 4-Fluorophenyl | 2,13(s, 3H), 6,90(m, 2H); 7,00(m, 2H) |
| 1.10 | n-Propyl | $-CH_2CH_2CH_2-O-$ | 4-Fluorophenyl | 2,15(s, 3H); 4,05(m, 2H); 4,25(m, 2H); 6,85(m, 2H); 6,95(m, 2H) |
| 1.11 | Ethyl | $-CH_2CH(CH_3)-O-$ | 4-Chlorophenyl | 2,13(s, 3H); 4,20(m, 2H); 4,60(m, 1H); 6,90(d, 2H); 7,20(d, 2H) |
| 1.12 | n-Propyl | $-CH_2CH(CH_3)-O-$ | 4-Chlorophenyl | 2,15(s, 3H); 4,20(m, 2H); 4,65(m, 1H); 6,90(d, 2H); 7,25(d, 2H) |
| 1.13 | Ethyl | $-CH_2CH_2CH_2CH_2-$ | 2-Thienyl | 2,13(s, 3H); 4,10(m, 2H); 6,80(m, 1H); 6,95(m, 1H); 7,15 (m, 1H) |
| 1.14 | n-Propyl | $-CH_2CH_2CH_2CH_2-$ | 2-Thienyl | 2,15(s, 3H); 4,10(m, 2H); 6,80(m, 1H); 6,95(m, 1H); 7,15(m, 1H) |
| 1.15 | Ethyl | $-CH_2-$ | 5-Chloro-2-thienyl | 2,13(s, 3H); 5,10(s, 2H); 6,85(m, 2H) |
| 1.16 | n-Propyl | $-CH_2-$ | 5-Chloro-2-thienyl | 2,15(s, 3H); 5,13(s, 2H); 6,83(m, 2H) |
| 1.17 | Ethyl | $-CH_2-$ | 3-Methyl-5-isox-azolyl | 2,15(s, 3H); 2,35(s, 3H); 5,10(s, 2H); 6,15(s, 1H) |
| 1.18 | n-Propyl | $-CH_2-$ | 3-Methyl-5-isox-azolyl | 2,15(s, 3H); 2,35(s, 3H); 5,10(s, 2H); 6,15(s, 1H) |
| 1.19 | Ethyl | $-CH_2CH_2OCH_2-$ | 3-Methylphenyl | 2,13(s, 3H); 2,35(s, 3H); 4,55(s, 2H); 7,05–7,30(m, 4H) |
| 1.20 | n-Propyl | $-CH_2CH_2OCH_2-$ | 3-Methylphenyl | 2,13(s, 3H); 2,35(s, 3H); 4,55(s, 2H); 7,05–7,30(m, 4H) |
| 1.21 | Ethyl | cis-$CH_2C(CH_3)=CH-$ | 4-Chlorophenyl | 1,90(s, 3H); 2,15(s, 3H); 4,60(s, 2H); 6,55(s, 1H); 7,15–7,35(m, 4H) |
| 1.22 | n-Propyl | cis-$CH_2C(CH_3)=CH-$ | 4-Chlorophenyl | 1,90(s, 3H); 2,15(s, 3H); 4,60(s, 2H); 6,55(s, 1H); 7,15–7,35(m, 4H) |
| 1.23 | Ethyl | $-CH_2CH_2CH_2-O-$ | 2,4-Dichlorophenyl | 2,15(s, 3H); 4,10(m, 2H); 4,30(m, 2H); 6,85(d, 1H); 7,15(dd, 1H); 7,35(d, 1H) |
| 1.24 | n-Propyl | $-CH_2CH_2CH_2-O-$ | 2,4-Dichlorophenyl | 2,15(s, 3H); 4,10(m, 2H); 4,30(m, 2H); 6,85(d, 1H); 7,15(dd, 1H); 7,35(d, 1H) |
| 1.25 | Ethyl | $-CH_2CH_2-O-$ | 4-Chlorophenyl | 2,13(s, 3H); 4,20(m, 2H); 4,40(m, 2H); 6,85(d, 2H); 7,25(d, 2H) |
| 1.26 | n-Propyl | $-CH_2CH_2-O-$ | 4-Chlorophenyl | 2,13(s, 3H); 4,20(m, 2H); 4,40(m, 2H); 6,85(d, 2H); 7,25(d, 2H) |
| 1.27 | Ethyl | $-CH_2CH_2-O-$ | 2,4-Difluorophenyl | 2,13(s, 3H); 4,25(m, 2H); 4,40(m, 2H); 6,70–7,00(m, 3H) |
| 1.28 | n-Propyl | $-CH_2CH_2-O-$ | 2,4-Difluorophenyl | 2,13(s, 3H); 4,25(m, 2H); 4,40(m, 2H); 6,70–7,00(m, 3H) |
| 1.29 | Ethyl | $-CH_2CH_2CH_2-O-$ | 2,4-Difluorophenyl | 2,13(s, 3H); 4,10(t, 2H); 4,30(t, 2H); 6,70–7,00(m, 3H) |
| 1.30 | n-Propyl | $-CH_2CH_2CH_2-O-$ | 2,4-Difluorophenyl | 2,13(s, 3H); 4,10(t, 2H); 4,30(t, 2H); 6,70–7,00 (m, 3H) |
| 1.31 | Ethyl | $-CH_2CH(CH_3)-O-$ | 4-Fluorophenyl | 2,15(s, 3H); 4,15(m, 2H); 4,55(m, 1H); 6,80–7,00(m, 4H) |
| 1.32 | n-Propyl | $-CH_2CH(CH_3)-O-$ | 4-Fluorophenyl | 2,15(s, 3H); 4,15(m, 2H); 4,55(m, 1H); 6,80–7,00(m, 4H) |
| 1.33 | Ethyl | $-CH_2CH_2-O-$ | 2,4-Dichlorophenyl | 2,15(s, 3H); 4,25(m, 2H); 4,45(m, 2H); 6,85(d, 1H); 7,15(dd, 1H); 7,35(d, 1H) |
| 1.34 | n-Propyl | $-CH_2CH_2-O-$ | 2,4-Dichlorophenyl | 2,15(s, 3H); 4,25(m, 2H); 4,45(m, 2H); 6,85(d, 1H); 7,15(dd, 1H); 7,35(d, 1H) |
| 1.35 | n-Propyl | $-CH_2CH_2CH_2-O-$ | 4-Chlorophenyl | 2,15(s, 3H); 4,05(t, 2H); 4,25(t, 2H); 6,80(m, 2H); 7,20(m, 2H) |

TABLE 2

$$\text{structure with } CH_3CH_2-S \text{ substituent, OH, N-O-A-Z-(X)}_n, R^1; \quad I\ (R^2-S(O)_m- = CH_3CH_2-S-)$$

| | R¹ | A | Z (X)ₙ | Physical data (¹H—NMR [ppm]; mp. [°C.]) |
|---|---|---|---|---|
| 2.01 | Ethyl | —CH₂CH(CH₃)—O— | 4-Chlorophenyl | 1,60(m, 1H); 4,20(m, 2H); 4,65(m, 1H); 6,80(d, 2H); 7,25(d, 2H) |
| 2.02 | n-Propyl | —CH₂CH(CH₃)—O— | 4-Chlorophenyl | 1,60(m, 1H); 4,20(m, 2H); 4,65(m, 1H); 6,80(d, 2H); 7,25(d, 2H) |
| 2.03 | Ethyl | —CH₂CH₂—O— | 2,4-Difluorophenyl | 1,60(m, 1H); 4,25(m, 2H); 4,40(m, 2H); 6,70–7,00(m, 3H) |
| 2.04 | n-Propyl | —CH₂CH₂—O— | 2,4-Difluorophenyl | 1,60(m, 1H); 4,25(m, 2H); 4,40(m, 2H); 6,70–7,00(m, 3H) |
| 2.05 | Ethyl | —CH₂CH₂CH₂—O— | 2,4-Difluorophenyl | 1,60(m, 1H); 4,10(t, 2H); 4,30(t, 2H); 6,70–7,00(m, 3H) |
| 2.06 | n-Propyl | —CH₂CH₂CH₂—O— | 2,4-Difluorophenyl | 1,60(m, 1H); 4,10(t, 2H); 4,30(t, 2H); 6,70–7,00(m, 3H) |
| 2.07 | Ethyl | —CH₂CH(CH₃)—O— | 4-Fluorophenyl | 1,60(m, 1H); 4,20(m, 2H); 4,55(m, 1H); 6,80–7,00(m, 4H) |
| 2.08 | n-Propyl | —CH₂CH(CH₃)—O— | 4-Fluorophenyl | 1,60(m, 1H); 4,20(m, 2H); 4,55(m, 1H); |
| 2.09 | Ethyl | —CH₂— | 5-Chlorothienyl | 1,60(m, 1H); 5,10(s, 2H); 6,83(m, 2H) |
| 2.10 | n-Propyl | —CH₂— | 5-Chlorothienyl | 1,60(m, 1H); 5,10(s, 2H); 6,83(m, 2H) |

TABLE 3

$$\text{structure with } CH_3CH_2CH_2-S \text{ substituent, OH, N-O-A-Z-(X)}_n, R^1; \quad I\ (R^2-S(O)_m- = CH_3CH_2-S-)$$

| | R¹ | A | Z (X)ₙ | Physical data (¹H—NMR [ppm]; mp. [°C.]) |
|---|---|---|---|---|
| 3.01 | Ethyl | —CH₂CH(CH₃)—O— | 4-Chlorophenyl | 0,75(m, 2H); 4,20(m, 2H); 4,65(m, 1H); 6,80(d, 2H); 7,25(d, 2H) |
| 3.02 | n-Propyl | —CH₂CH(CH₃)—O— | 4-Chlorophenyl | 0,75(m, 2H); 4,20(m, 2H); 4,65(m, 1H); 6,80(d, 2H); 7,25(d, 2H) |
| 3.03 | Ethyl | —CH₂CH₂—O— | 2,4-Difluorophenyl | 0,75(m, 2H); 4,25(m, 2H); 4,40(m, 2H); 6,70–7,00(m, 3H) |
| 3.04 | n-Propyl | —CH₂CH₂—O— | 2,4-Difluorophenyl | 0,75(m, 2H); 4,25(m, 2H); 4,40(m, 2H); 6,70–7,00(m, 3H) |
| 3.05 | Ethyl | —CH₂CH₂CH₂—O— | 2,4-Difluorophenyl | 0,75(m, 2H); 4,10(t, 2H); 4,25(t, 2H); 6,70–7,00(m, 3H) |
| 3.06 | n-Propyl | —CH₂CH₂CH₂—O— | 2,4-Difluorophenyl | 0,75(m, 2H); 4,10(t, 2H); 4,25(t, 2H); 6,70–7,00(m, 3H) |
| 3.07 | n-Propyl | —CH₂— | 5-Chlorothienyl | 0,75(m, 2H); 5,10(s, 2H); 6,83(m, 2H) |

The cyclohexenone oxime ethers I are suitable as herbicides, in particular for controlling plant species from the *Gramineae* family (grasses). In general, they are tolerated and are thus selective in broad-leaved crops and in monocotyledon plants which do not belong to the *Gramineae*, in particular in corn and rice. Some derivatives of the compounds I may, however, also exhibit selectivity in *Gramineae*, so that undesirable grasses can be selectively controlled.

The cyclohexenone oxime ethers I or the herbicides containing them can be applied, for example, in the form of directly sprayable solutions, powders, suspensions, including concentrated aqueous, oily and other suspensions and dispersions, emulsions, oil dispersions, pastes, dusting agents, broadcasting agents or granules, by spraying, nebulizing, dusting, broadcasting or pouring. The application forms depend on the intended uses; they should in any case ensure a very fine distribution of the novel active ingredients.

The compounds I are suitable in general for the preparation of directly sprayable solutions, emulsions, pastes or oil dispersions. Suitable inert additives are mineral oil fractions having a medium to high boiling point, such as kerosene or diesel oil, as well as coal tar oils and oils of vegetable or animal origin, aliphatic, cyclic and aromatic hydrocarbons, eg. toluene, xylene, paraffin, tetrahydronaphthalene, alkylated naphthalenes or derivatives thereof, methanol, ethanol, propanol, butanol, cyclohexanol, cyclohexanone, chlorobenzene or isophorone, or strongly polar solvents, such as N,N-dimethylformamide, dimethyl sulfoxide, N-methylpyrrolidone or water.

Aqueous application forms can be prepared from emulsion concentrates, dispersions, pastes, wettable powders or water-dispersible granules by adding water. For the preparation of emulsions, pastes or oil dispersions, the substrates, as such or dissolved in an oil or solvent, can be homogenized in water by means of wetting agents, adherents, dispersants or emulsifiers. However, concentrates which consist of active ingredient, wetting agents, adherents, dispersants or emulsifiers and possibly solvents or oil and which are suitable for dilution with water can also be prepared.

Suitable surfactants are alkali metal, alkaline earth metal and ammonium salts of aromatic sulfonic acids, for example lignin-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and of fatty alcohol glycol ethers, condensates of sulfonated naphthalene and its derivatives with formaldehyde, condensates of naphthalene or of naphthalenesulfonic acids with phenol and formaldehyde, polyoxyethylene octylphenol ethers, ethoxylated isooctyl-, octyl- or nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene, lauryl alcohol polyglycol ether acetate, sorbitol esters, ligninsulfite waste liquors or methylcellulose.

Powders, broadcasting agents and dusting agents can be prepared by mixing or milling the active ingredients together with a solid carrier.

Granules, for example coated, impregnated and homogeneous granules, can be prepared by binding the active ingredients to solid carriers. Solid carriers are minerals such as silica gel, silicas, silicates, talc, kaolin, limestone, lime, chalk, bole, loess, clay, dolomite, kieselguhr, calcium sulfate, magnesium sulfate and magnesium oxide, milled plastics, fertilizers, such as ammoniumsulfate, ammoniumphosphate, ammoniumnitrate and ureas, and vegetable products, such as grain flour, bark meal, wood meal and. nutshell meal, cellulosic powders or other solid carriers.

The formulations contain in general from 0.01 to 95, preferably from 0.5 to 90, % by weight of active ingredient. The active ingredients are used in a purity of from 90 to 100%, preferably from 95 to 100% (according to the NMR spectrum).

Examples of such formulations are:

I. A solution of 20 parts by weight of compound No. 1.03 in a mixture consisting of 80 parts by weight of xylene, 10 parts by weight of the adduct of from 8 to 10 mol of ethylene oxide with 1 mol of N-monoethanololeamide, 5 parts by weight of the calcium salt of dodecylbenzenesulfonic acid and 5 parts by weight of the adduct of 40 mol of ethylene oxide with I mol of castor oil. By finely distributing the mixture in 100,000 parts by weight of water, a dispersion which contains 0.02% by weight of the active ingredient is obtained.

II. A dispersion of 20 parts by weight of compound No. 1.05 in a mixture consisting of 40 parts by weight of cyclohexanone, 30 parts by weight of isobutanol and 20 parts by weight of the adduct of 70 mol of ethylene oxide with 1 mol of isoocytlphenol and 10 parts by weight of the adduct of 40 mol of ethylene oxide with 1 mol of castor oil. A mixture of this dispersion with 100,000 parts by weight of water contains 0.02% by weight of the active ingredient.

III. A dispersion of 20 parts by weight of compound No. 1.07 in a mixture consisting of 25 parts by weight of cyclohexanone, 65 parts by weight of a mineral oil fraction boiling within a range from 210° to 280° C. and 10 parts by weight of the adduct of 40 mol of ethylene oxide with 1 mol of castor oil. A mixture of this dispersion with 100,000 parts by weight of water contains 0.02% by weight of the active ingredient.

IV. A mixture, milled in a hammer mill, of 20 parts by weight of compound No. 1.09, 3 parts by weight of the sodium salt of diisobutylnaphthalene-α-sulfonic acid, 17 parts by weight of the sodium salt of a ligninsulfonic acid obtained from a sulfite waste liquor and 60 parts by weight of silica gel powder. By finely distributing the mixture in 20,000 parts by weight of water, a spray liquor which contains 0.1% by weight of the active ingredient is obtained.

V. An intimate mixture of 3 parts by weight of compound No. 1.11 and 97 parts by weight of finely divided kaolin. This dusting agent contains 3% by weight of active ingredient.

VI. A stable oily dispersion of 20 parts by weight of compound No. 1.01, 2 parts by weight of the calcium salt of dodecylbenzenesulfonic acid, 8 parts by weight of fatty alcohol polyglycol ether, 2 parts by weight of the sodium salt of a phenolsulfonic acid/urea/formaldehyde condensate and 68 parts by weight of a paraffinic mineral oil.

The herbicides or the active ingredients can be applied by the preemergence or postemergence method. If the active ingredients are less well tolerated by certain crops, it is possible to use application methods in which the herbicides are sprayed with the aid of the sprayers in such a way that the leaves of the sensitive crops are as far as possible not touched, whereas the active ingredients reach the leaves of undesirable plants growing underneath or the uncovered soil surface (post-directed, lay-by).

The application rates of active ingredient are from 0.001 to 3.0, preferably from 0.01 to 1, kg/ha of active ingredient (a.i.), depending on the aim of control, the season, the target plants and the stage of growth.

Because of the wide range of application methods, the cyclohexenone oxime ethers I or agents containing them can be used in a further number of crops for eliminating undesirable plants. Examples of suitable crops are the following:

| Botanical name | Common name |
|---|---|
| *Allium cepa* | onions |
| *Ananas comosus* | pineapples |
| *Arachis hypogaea* | peanuts (groundnuts) |
| *Asparagus officinalis* | asparagus |
| *Beta vulgaris* spp. *altissima* | sugarbeets |
| *Beta vulgaris* spp. *rapa* | fodder beets |
| *Brassica napus* var. *napus* | rapeseed |
| *Brassica napus* var. *napobrassica* | swedes |
| *Brassica rapa* var. *silvestris* | beets |
| *Camellia sinensis* | tea plants |
| *Carthamus tinctorius* | safflower |
| *Carya illinoinensis* | pecan trees |
| *Citrus limon* | lemons |
| *Citrus sinensis* | orange trees |
| *Coffea arabica* (*Coffea canephora*, *Coffea liberica*) | coffee plants |
| *Cucumis sativus* | cucumbers |
| *Cynodon dactylon* | Bermuda grass |
| *Daucus carota* | carrots |
| *Elaeis guineensis* | oil palms |
| *Fragaria vesca* | strawberries |
| *Glycine max* | soybeans |
| *Gossypium hirsutum* (*Gossypium arboreum*, *Gossypium herbaceum*, *Gossypium vitifolium*) | cotton |
| *Helianthus annuus* | sunflowers |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lens culinaris* | lentils |

-continued

| Botanical name | Common name |
| --- | --- |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Musa* spp. | banana plants |
| *Nicotiana tabacum* (*N. rustica*) | tobacco |
| *Olea europaea* | olive trees |
| *Oryza sativa* | rice |
| *Phaseolus lunatus* | limabeans |
| *Phaseolus vulgaris* | snapbeans, green beans, dry beans |
| *Picea abies* | Norway spruce |
| *Pinus* spp. | pine trees |
| *Pisum sativum* | English peas |
| *Prunus avium* | cherry trees |
| *Prunus persica* | peach trees |
| *Pyrus communis* | pear trees |
| *Ribes sylvestre* | redcurrants |
| *Ricinus communis* | castor-oil plants |
| *Saccharum officinarum* | sugar cane |
| *Secale cereale* | rye |
| *Solanum tuberosum* | Irish potatoes |
| *Sorghum bicolor* (*s. vulgare*) | sorghum |
| *Theobroma cacao* | cacao plants |
| *Trifolium pratense* | red clover |
| *Triticum aestivum* | wheat |
| *Triticum durum* | durum wheat |
| *Vicia faba* | tick beans |
| *Vitis vinifera* | grapes |
| *Zea mays* | Indian corn, sweet corn, maize |

To extend the action spectrum and to achieve synergistic effects, the cyclohexenone oxime ethers I can be mixed and applied together with a large number of members of other groups of herbicidal or growth-regulating active ingredients. Examples of components for the mixture are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives which carry, for example, carboxyl or carbimino in the 2-position, quinolinecarboxylic acid derivatives, imidazolinones, sulfonamides, sulfonylureas, aryloxy- and hetaryloxyphenoxypropionic acids and their salts, esters and amides and others.

It may also be useful if the compounds I, alone or in combination with other herbicides, are also applied as a mixture with further crop protection agents, for example with agents for controlling pests, phytopathogenic fungi or bacteria. The miscibility with mineral salt solutions which are used for eliminating nutrient and trace element deficiencies is also of interest. It is also possible to add nonphytotoxic oils and oil concentrates.

PREPARATION EXAMPLES

2-[1-[4-trans-(4-Fluorophenyl)-but-3-enyloximino]-propyl]-3-hydroxy-5-(1-methylthiocyclopropyl)-2-cyclohexen-1-one (compound 1.1)

A mixture of 2.0 g (7.9 mmol) of 3-hydroxy-5-(1-methylthiocyclopropyl)-2-propionyl-2-cyclohexen-1-one, 1.6 g (9.0 mmol) of 0-[4-trans-(4-fluorophenyl)-but-3-enyl]-hydroxylamine and 100 ml of methanol was stirred for 24 hours and then evaporated down under reduced pressure. Yield: 100%

$^1$H-NMR (200 MHz, in CDCl$_3$): δ [ppm]=0.77 (m, 2H); 0.97 (m, 2H); 1.10 (t, 3H); 1.60 (m, 1H); 2.13 (s, 3H); 2.40–2.80 (m, 6H); 2.90 (q, 2H); 4.17 (t, 2H); 6.10 (dt, 1H); 6.43 (d, 1H); 7.00 (m, 2H); 7.30 (m, 2H); 14.80 (s, 1H).

2-[1-[4-trans-(4-Chlorophenyl)-but-3-enyloximino]-propyl]-3-hydroxy-5-(1-methylthiocyclopropyl)-2-cyclohexen-1-one (compound 1.3)

A mixture of 2.0 g (7.9 mmol) of 3-hydroxy-5-(1-methylthiocyclopropyl)-2-propionyl-2-cyclohexen-1-one, 1.8 g (9.0 mmol) of O-[4-trans-(4-chlorophenyl)-but-3-enyl]-hydroxylamine and 100 ml of methanol was stirred for 24 hours and then evaporated down under reduced pressure. Yield: 100%

$^1$H-NMR (200 MHz, in CDCl$_3$): δ [ppm]=0.77 (m, 2H); 0.97 (m, 2H); 1.10 (t, 3H); 1.60 (m, 1H); 2.13 (s, 3H); 2.40–2.80 (m, 6H); 2.90 (q, 2H); 4.20 (t, 2H); 6.20 (dt, 1H); 6.43 (d, 1H); 7.27 (s, 4H); 14.70 (s, 1H).

USE EXAMPLES

The herbicidal action of the cyclohexenone oxime ethers of the formula I was demonstrated by greenhouse experiments:

The vessels used were plastic flowerpots containing loamy sand with about 3.0% of humus as a substrate. The seeds of the test plants were sown separately according to species.

In preemergence treatment, the active ingredients suspended or emulsified in water were applied directly after sowing, by means of finely distributing nozzles. The vessels were lightly watered in order to promote germination and growth and were then covered with transparent plastic covers until the plants had begun to grow. This covering ensures uniform germination of the test plants, unless germination had been adversely affected by the active ingredients.

For the postemergence treatment, the test plants were initially grown in the test vessels or were planted in the test vessels a few days beforehand. The active ingredients suspended or emulsified in water were not applied until a height of growth of from 3 to 15 cm had been reached, depending on the form of growth. The application rate for the postemergence treatment was 0.25 kg/ha of a.i.

The plants were kept at 10°–25° C. or 20°–35° C., according to species. The test period extended over 2 to 4 weeks. During this time, the plants were tended and their response to the individual treatments was evaluated.

Evaluation was based on a scale of from 0 to 100. 100 means no emergence of the plants or complete destruction of at least the above-ground parts and 0 means no damage or normal growth.

The plants used in the greenhouse experiments consisted of the following species:

| Botanical name | Common name |
| --- | --- |
| *Echinochloa crus-galli* | barnyard grass |
| *Setaria faberii* | Giant foxtail |
| *Setaria viridis* | Green foxtail |

The result showed that gramineous plants can be very readily controlled postemergence with compound No. 1.05.

We claim:

1. Cyclohexenone oxime ether of the formula I

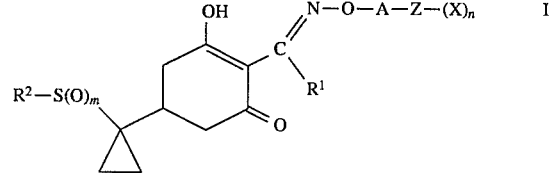

in which the substituents have the following meanings:

n is from 0 to 5;

m is from 0 to 2;

$R^1$ is $C_1$–$C_6$-alkyl;

$R^2$ is $C_1$–$C_4$-alkyl or benzyl;

A is $C_1$–$C_6$-alkylene or $C_3$–$C_6$-alkenylene where these groups may carry from one to three $C_1$–$C_3$-alkyl groups and/or halogen atoms, or a $C_3$–$C_6$-alkylene or $C_4$–$C_6$-alkenylene group which, is unsubstituted or is substituted by from one to three $C_1$–$C_3$-alkyl groups and in which one methylene group is replaced with an oxygen or sulfur atom, a sulfoxyl or sulfonyl group or a group —N($R^a$)—, where $R^a$ is hydrogen, $C_1$–$C_4$-alkyl, $C_3$–$C_6$-alkenyl or $C_3$–$C_6$-alkynyl;

Z is phenyl, a 5-membered heteroaromatic radical having from one to three nitrogen atoms and/or one oxygen or sulfur atom or a 6-membered heteroaromatic radical having from one to four nitrogen atoms, and X is nitro, cyano, halogen, $C_1$–$C_4$-alkyl, partially or completely halogenated $C_1$–$C_4$-alkyl, $C_1$–$C_4$-alkoxy, $C_1$–$C_4$-alkylthio, partially or completely halogenated $C_1$–$C_4$-alkoxy, carboxyl, $C_1$–$C_4$-alkoxycarbonyl, benzyloxycarbonyl, phenyl or pyridyl, where the aromatic radicals may be unsubstituted or carry from one to three of the following substituents: nitro, cyano, halogen, $C_1$–$C_4$-alkyl, partially or completely halogenated $C_1$–$C_4$-alkyl, $C_1$–$C_4$-alkoxy, $C_1$–$C_4$-alkylthio, partially or completely halogenated $C_1$–$C_4$-alkoxy, carboxyl, $C_1$–$C_4$-alkoxycarbonyl, benzyloxycarbonyl or an amino group —$NR^bR^c$, where $R^b$ is hydrogen, $C_1$–$C_4$-alkyl, $C_3$–$C_6$-alkenyl or $C_3$–$C_6$-alkynyl and $R^c$ is hydrogen, $C_1$–$C_4$-alkyl, $C_3$–$C_6$-alkenyl, $C_3$–$C_6$-alkynyl, $C_1$–$C_6$-acyl or benzoyl which my be unsubstituted or in its turn carry from one to three of the following radicals: nitro, cyano, halogen, $C_1$–$C_4$-alkyl, $C_1$–$C_4$-alkoxy, $C_1$–$C_4$-alkylthio, $C_1$–$C_4$-haloalkyl, $C_1$–$C_4$-haloalkoxy and/or $C_1$–$C_4$-alkoxycarbonyl, and its agriculturally useful salts and esters of $C_1$–$C_{10}$-carboxylic acids and inorganic acids.

2. A herbicidal composition containing a liquid or solid carrier and a herbicidal amount of one or more cyclohexenone oxime ethers I as defined in claim 1.

3. A method for controlling undesirable plant growth, wherein a herbicidal amount of a cyclohexenone oxime ether I as defined in claim 1 is allowed to act on plants or their habitat or on seeds.

4. A cyclohexenone oxmie ether of the formula I

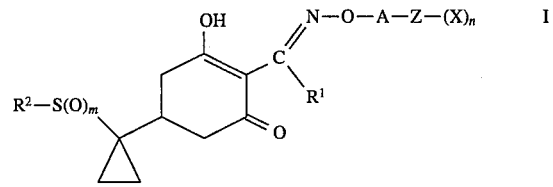

as defined in claim 1, in which the substituents have the following meanings:

n is from 0 to 2;

m is 0;

$R^1$ is $C_1$–$C_4$-alkyl;

$R^2$ is $C_1$–$C_3$-alkyl;

A is $C_1$–$C_4$-alkylene, or $C_3$- or $C_4$-alkenylene, where these groups may carry from one to three $C_1$–$C_3$-alkyl groups; or a three- to six-membered alkylene chain which is unsubstituted or is substituted by from one to three $C_1$–$C_3$-alkyl groups and in which chain one methylene group is replaced with an oxygen atom;

Z is phenyl or a 5-membered heteroaromatic radical having from one to three nitrogen atoms and/or one oxygen or sulfur atom, and Z is nitro, halogen, $C_1$–$C_4$-alkyl or partially or completely halogenated $C_1$–$C_4$-alkyl.

* * * * *